(12) United States Patent
Moore et al.

(10) Patent No.: US 7,171,964 B2
(45) Date of Patent: Feb. 6, 2007

(54) INSTANT CHEMICAL BASED FLEXIBLE OXYGEN IN A NON-PRESSURIZED FLEXIBLE OR RIGID CONTAINMENT SYSTEM

(76) Inventors: Bert K. Moore, 4579 Jennifer St., Boise, ID (US) 83704; Steven Hatten, 1910 University Dr., Boise, ID (US) 83725; Kevin Haight, 1910 University Dr., Boise, ID (US) 83725; Nathaniel Haro, 1910 University Dr., Boise, ID (US) 83725; Frank Fosella, 2507 S. Swallowtail La., Boise, ID (US) 83706

( * ) Notice: Subject to any disclaimer, the term of this patent is extended or adjusted under 35 U.S.C. 154(b) by 75 days.

(21) Appl. No.: 10/865,455

(22) Filed: Jun. 9, 2004

(65) Prior Publication Data

US 2005/0022810 A1    Feb. 3, 2005

Related U.S. Application Data

(60) Provisional application No. 60/558,809, filed on Apr. 1, 2004, provisional application No. 60/564,539, filed on Apr. 21, 2004, provisional application No. 60/477,452, filed on Jun. 9, 2003.

(51) Int. Cl.
A61M 15/00 (2006.01)

(52) U.S. Cl. .................. 128/202.26; 128/205.27; 128/205.29; 128/205.21; 422/120; 422/129

(58) Field of Classification Search .......... 128/202.26, 128/205.27, 205.28, 205.29, 206.12, 205.12, 128/205.21; 422/120, 129
See application file for complete search history.

(56) References Cited

U.S. PATENT DOCUMENTS

| 3,574,561 | A | * | 4/1971 | Nickerson et al. .......... 422/106 |
|---|---|---|---|---|
| 3,615,252 | A | * | 10/1971 | DiPietro ..................... 422/120 |
| 3,733,008 | A | * | 5/1973 | Churchill et al. ............. 222/6 |
| 3,868,225 | A | * | 2/1975 | Tidd .......................... 422/122 |
| 3,955,931 | A | * | 5/1976 | Thompson .................. 422/165 |
| 3,971,372 | A | * | 7/1976 | Lenk et al. ............ 128/202.26 |
| 4,278,637 | A | * | 7/1981 | McBride ..................... 422/122 |
| 4,294,244 | A | * | 10/1981 | Pasternack ............. 128/202.26 |
| 4,491,130 | A | * | 1/1985 | Pasternack ............. 128/202.26 |
| 4,526,758 | A | * | 7/1985 | Alengoz et al. ............ 422/122 |
| 4,536,370 | A | * | 8/1985 | Hahn ......................... 422/120 |
| 4,548,730 | A | * | 10/1985 | Koslow ................. 252/186.43 |
| 4,597,917 | A | * | 7/1986 | Lunsford .................... 261/153 |
| 5,029,578 | A |   | 7/1991 | Swiatosz |
| 5,222,479 | A | * | 6/1993 | Brauer et al. .......... 128/202.26 |
| 5,267,646 | A |   | 12/1993 | Inoue et al. |
| 5,423,421 | A |   | 6/1995 | Inoue et al. |
| 5,804,146 | A |   | 9/1998 | Heyer et al. |
| 5,823,181 | A | * | 10/1998 | Shih ..................... 128/202.26 |
| 5,967,308 | A |   | 10/1999 | Bowen |
| 6,036,004 | A |   | 3/2000 | Bowen |
| 6,041,778 | A | * | 3/2000 | Swann et al. .......... 128/201.25 |
| 6,123,069 | A |   | 9/2000 | Davis |

(Continued)

Primary Examiner—Henry Bennett
(74) Attorney, Agent, or Firm—Robert L. Shaver; Dykas, Shaver & Nipper, LLP

(57) ABSTRACT

The invention is a portable, non-pressurized oxygen generation device. A first chamber holds an oxygen liberating chemical, and a catalyst from a second chamber begins the oxygen liberating reaction when the two chemicals mix. The chemicals are pre-measured, and oxygen generation can begin within seconds of activation.

30 Claims, 8 Drawing Sheets

U.S. PATENT DOCUMENTS 6,143,251 A * 11/2000 Beller et al. ................. 422/120
6,155,254 A * 12/2000 Evrard et al. .......... 128/202.26
6,267,114 B1    7/2001 Ueno
6,279,571 B1 * 8/2001 Meckes ................. 128/201.22
6,443,149 B1 * 9/2002 Wise ..................... 128/202.26
6,508,605 B1    1/2003 Cheng

* cited by examiner

INSTANT CHEMICAL BASED FLEXIBLE OXYGEN IN A NON-PRESSURIZED FLEXIBLE OR RIGID CONTAINMENT SYSTEM

PRIORITY

This application claims the priority dates of the provisional applications entitled Weak Seal Oxygen Generation Flexible IV System filed by Anthony J. Senn, et al. on Jun. 9, 2003 with application Ser. No. 60/477,452, Instant Chemical Based Flexible Oxygen in a Non-Pressurized Flexible or Rigid Containment System filed by Bert K. Moore, et al. on Apr. 21, 2004 with application Ser. No. 60/564,539, and Oxygen Generation Unit filed by Steven Hatten, et al. on Apr. 1, 2004 with application Ser. No. 60/558,809, the disclosures of which are incorporated herein by reference.

BACKGROUND OF THE INVENTION

1. Field of the Invention

The present invention is generally related to portable oxygen producing devices, and more particularly to a self contained, non-pressurized, flexible portable oxygen system.

2. Background Information

There are a number of situations in which a source of oxygen would be an essential lifesaving tool. This could include a situation where a person is in a burning building and a supply of oxygen, even if only for a few minutes, would increase his or her chances of escape from the smoke filled building. This could apply to office workers, rescue personnel or police.

Another situation in which emergency oxygen would be useful is in response to an emergency situation, such as an environment filled with poisonous gases. This could occur in a chemical plant from a rupture of a tank, or could occur on a battlefield from the use of chemical weapons. In such a case, having a quickly available supply of oxygen, which has been conveniently stored and has a long shelf life, would be a lifesaver. Other situations in which an emergency supply of oxygen would be useful would include use by pilots who may need to clear their head when flying at a higher elevation, first aid situations in which oxygen may need to be administered in the field before the person is picked up by oxygen equipped rescue personnel, at home where a person may wish to administer oxygen in response to shortness of breath, heart arrhythmia, heart attack, or stroke.

The prior art includes many oxygen generation devices. Many of them involve a rigid canister in which oxygen gas is compressed, and from which it can be released for breathing. Other prior art oxygen generation systems are reaction vessels, in which chemicals of various types can be added in order to set up a reaction that generates oxygen. The problem with compressed oxygen is that these systems are expensive, heavy, and not practical for most people to have on hand. Devices based on a reaction vessel are impractical if the reaction vessel is bulky and hard to carry, and if the chemicals take any more than the absolute minimum of time and effort to add and mix for use. A person cannot hold their breath very long while preparing such a canister, measuring ingredients, and adding the ingredients. A reaction vessel which takes more than ten (10) seconds to access, activate, and begin receiving oxygen is not very effective. One which takes several minutes to access, activate, and begin receiving oxygen is not particularly practical in the situations that are described above.

A portable emergency oxygen generation system needs to be small in size, have a long shelf life, be easy to activate, but which does not activate accidentally, and must generate breathable oxygen within a few seconds of activation. Anything that takes more than even five seconds is not effective in certain situations. None of the prior art oxygen generation devices has these features.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

These, and other objects are achieved in the oxygen generating system of the invention.

One embodiment of the invention includes a reaction chamber that is partially filled with a first reaction material. The portable oxygen generation system further includes a second chamber that is adjacent to the first chamber. The second chamber includes a pre-measured volume of a second reaction material. The first and second reaction materials are selected so that oxygen is generated when the first and second reaction materials are mixed. The system includes an oxygen release tube that is positioned within the reaction chamber so as to be above the level of the first material. The reaction chamber, with the first reaction material that it encloses, is designed with the oxygen release tube so that the reaction chamber may be in any spatial orientation and the end of the oxygen release tube will be above the level of the first reaction material. An activation means is included that is configured to immediately activate oxygen generation by opening the second chamber to allow immediate mixing of the second material with the first material. This results in immediate and continuous oxygen production from the mixing of the two materials and their subsequent reactions. A delivery device is included that delivers oxygen from the reaction chamber to a user. The size of the reaction chamber and the volume of materials determine the duration of oxygen generation. Typical times for the device are about twenty minutes of oxygen generation. Longer oxygen generation can be achieved by using more of the first and second materials and a larger reaction vessel.

One embodiment of the invention includes a reaction chamber that is a semi-rigid material. In this version of the device, the second chamber is a breakable ampule containing a quantity of the second reaction material. The ampule is supported in an ampule bracket within the reaction chamber. The activation means of this system is an ampule breaking device. The ampule breaking device is typically a plunger pin that may be spring loaded and fitted with a locking device for preventing unwanted activation. When the locking device is disengaged, the ampule may be broken by pressing down on the plunger, causing the ampule to be broken and allowing the contents of the ampule to mix freely with the contents of the reaction vessel. This system includes an oxygen release tube that extends from the reaction chamber wall to the approximate center of the wall. The oxygen release tube has a tube opening, and because the first material only partially fills the vessel, the tube opening remains above the level of the first material when the reaction vessel is in any orientation. The oxygen release tube is typically attached at one end to the reaction chamber wall and extends through the chamber wall, where a hose barb allows it to attach to delivery tubing. This design further includes an external carrying pouch, in which the oxygen generation system can be stored and transported where it is available for use. The action to generate oxygen is an exothermal one. The external carrying pouch thus serves the important function of isolating the user from the heat generated in the reaction.

Another version of the oxygen generation system includes a reaction chamber that is a flexible pouch. One version of this design includes an external hard case that surrounds or partially surrounds the flexible pouch. The reaction chamber of the vessel is a chamber inside the flexible pouch. The second chamber is also a chamber within the flexible pouch, which is separated from the reaction chamber by a seal. Squeezing the flexible pouch may rupture the seal between these vessels. The semi-rigid outer container of this embodiment may have openings on the sides that allow the flexible container to be accessed for squeezing the bag to activate the oxygen generation reaction. In the version of the device that includes a flexible pouch, the oxygen release tube extends from a reaction chamber wall to the approximate center of the reaction vessel and because of the level of the first material in the reaction vessel, the tube opening of the oxygen release tube remains about the level of the first material when the reaction vessel is in an spatial orientation. The oxygen release tube may be a flexible tube that includes a float at the end that assists it in keeping it above the liquid of the reaction vessel. This version of the device would also preferably contain an outer containment pouch for holding the flexible bladder during use of the system.

Also included in the portable oxygen generation system of the invention is a delivery system that is configured to deliver the oxygen that is created within the flexible bladder, to a user.

Typically, the delivery system of the device will include a conduit in the form of a plastic tube for delivering oxygen from the flexible bladder to the user. At one end of the conduit is located an oxygen delivery mask, which may be worn by the user for breathing oxygen. A nasal canula would also be a possible delivery device.

The portable oxygen generation system of the invention functions as described above, but alternate embodiments may contain additional features. These can include a humidifying chamber. When oxygen is generated in the flexible bladder, it is part of an exothermic reaction and enters the conduit and the oxygen delivery mask in a fairly warm and dry state. An inline chamber in the conduit may be helpful to cool the oxygen before it reaches the delivery mask. It also has the effect of adding some humidity to the oxygen. If the humidifying chamber is structured for bubbling, observing bubbles passing through the humidifying chamber serves to assure the user that oxygen is being generated and passing through the conduit to the delivery mask.

Another feature that is desirable in certain embodiments of the invention is to have a filter located inline between the user and the flexible bladder. This filter can serve as a check valve, and allow oxygen gas but not liquid from the flexible bladder pass into the delivery of the conduit and delivery mask. Such a check valve can be made of a hydrophobic material which allows air to pass, but does not allow water to pass. Certain types of hydrophobic filters are basically filter paper that is coated with Teflon, or a similar material. In filters such as these, liquid water absolutely does not pass through the filter. Other types of check valves would also perform this function, such as check valves for preventing liquid flow in a line.

It may be further desirable to have a chemical filter inline in the conduit between the flexible bladder and the delivery mask. The flexible filter would be provided to absorb odors or product chemicals from the exothermic reaction. To achieve this purpose, the chemical filter could contain an activated charcoal unit through which the generated oxygen passes. Gasses other than oxygen would be absorbed and/or reacted by the activated charcoal, leaving only pure oxygen to pass to the user. A foam or fibrous portion of the filter would also be desirable.

Another feature that may be utilized is an oxygen flow indicator. This would be an inline indicator, typically one that changes color, to indicate the flow of oxygen in the tube.

Another feature of the oxygen generation system of the invention is an outer pouch. An outer pouch serves several functions, and can be quite important for the oxygen generation system. One function it serves is that it protects the flexible bladder from external injury, so that it is less likely to be ripped or torn. The outer pouch is also preferably liquid proof, and thus would serve as a containment vessel if the liquid in the flexible bladder leaked. Another function of the outer pouch is to act as a holder for the flexible bladder while the flexible bladder is generating oxygen. Many oxygen generation reactions are exothermic reactions that can produce a considerable amount of heat. Thus, it might be uncomfortable for a user to hold the flexible bladder while it is generating oxygen. The outer pouch serves the purpose of providing an insulating carrying case, which insulates the user from the heat generated during oxygen production. The outer pouch can include a shoulder strap, or a handle. It can also be provided with a hole through which the air line can pass, so that the outer pouch and the flexible bladder can be placed in an oxygen generation cabinet.

Depending on the chemicals selected to produce oxygen in the oxygen generation system, the flexible bladder may be configured to have three chambers. Each of these chambers is separated from the others by a separation membrane. These separation membranes are made of a flexible sheet of material, which ruptures when a sufficient amount of pressure is applied to it.

The purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

A delivery device is configured for use with the flexible bladder. The delivery device is not attached to the bladder until use of the device is desired. As will be described later in detail the configuration of the delivery device and the connection of the delivery device to the flexible bladder can be varied according to the necessities and preferences of the potential users and customers.

Once the flexible bladder of the present invention has been properly constructed and filled, it may be stored in a designated location or it may be assembled for use. In order to use this embodiment of the invention, the delivery device must be attached to the flexible bladder. Connection between the flexible bladder and the delivery device is typically performed by attaching a hose end of the delivery device to the flexible bladder. Rupturing the ampule or squeezing the flexible container bag will then allow the materials in the various chambers to mix together so as to allow the production of oxygen within the reaction chamber or flexible bladder bag.

In storage, the various configurations of the device may be stored as a single unit. In a three-chamber design, a liquid chamber is filled with sterilized liquid so as to prevent bacterial contamination. The first compound may be sodium percarbonate, hydrogen peroxide, or a number of other oxygen generating chemicals. The second compound may be manganese powder, which is preferably reagent grade manganese dioxide. In the stored position, the contents of the first and second chambers are separated by the ampule wall or by the weak seal separations between the various chambers. When these chemicals are separated, no chemical reaction will take place, and the oxygen generation device can be simply stored. The exact formulation of the weak seal and flexible bladder walls can also be variously embodied. In some situations the weak wall may simply be a weakened seam, or aperture, which is configured to open and allow integration and mixing of the various chemicals within the device. In other embodiments the whole wall may be configured to allow leakage when pressure is applied to the device.

In order to use the device of this embodiment, a delivery device may be attached to the rigid outer container or inserted into the flexible bladder by a medical spike-type apparatus that is hollowed to provide transport of material out of the liquid chamber. After the attachment is made, the device may be activated by breaking the ampule or squeezing the bladder. In one embodiment, when the device is squeezed, a quantity of liquid will travel through a check valve into a humidifier chamber. When a sufficient quantity of liquid has entered into this chamber to reach the liquid line, the tubing clamp below the liquid chamber is cut off to prevent further flow of material up into the delivery device. As liquid is displaced out of the liquid chamber into the humidifier chamber, it is replaced with air through the liquid chamber. Once this has occurred, the entire flexible bladder may then be squeezed.

In the case of the bladder with chambers separated by weak seals, when the bladder is squeezed, the differences in volumes on the sides of the chambers and between the chambers create an uneven force along the walls. These weak seal walls will then rupture and fail when the chambers are pressed. When this occurs, a mixture of materials between the varying chambers exists, and as this takes place, oxygen is produced as the chemical reaction between the various items within the chambers occurs. Once the materials have been mixed, and oxygen begins to be formed, the oxygen can be exited from the flexible bladder and delivered through the device to a mask, nasal canula or other delivery system to an individual. This is done by opening the tubing clamp. When the tubing clamp is open, oxygen will flow through the conduit, past the check valve into the humidifier chamber. The presence of bubbles ascending to the liquid line within the humidifier chamber gives positive identification to the individual utilizing the device that oxygen is being produced and is passing through the chamber. The mixture of liquid with the oxygen also makes these things more palatable.

Along the delivery device conduit may be located a hydrophobic filter chamber that allows the oxygen to pass through for use but prevents the passage of liquid through. This is a safety feature, which prevents unwanted aspiration of liquid from the material into the respiratory system of the individual utilizing the device. Another design to prevent liquid from entering the conduit is to utilize a liquid trap in which liquid entering with the oxygen is collected in a cup, and only gas passes out of the liquid trap.

The present invention provides a dependable portable emergency oxygen system that can have an indefinite shelf life and provide immediate capabilities for oxygen production and use without the requirements of filling with liquid, filling with water, adding catalysts, or other things that may be required in other methods. The present invention can be variously modified to use in a variety of environments such as emergency medical situations, armed conflicts, field use by military and rescue personnel, home first aid, building and tank evacuation, mountain climbing, airplane flying, and other uses. In addition, because the devices are fully self-contained, they could be utilized as a backup in other activities where a respirator is used. Due to the fact that the device is made of non-compressed materials, they are much less bulky and less of an environmental and ecological hazard than those devices that use compressed gas in cylinders.

In various embodiments, depending upon the requirements of the user, the rate of oxygen flow and production may be varied by the configuration of the chambers within the device or by the use of flow rate valves within the delivery device.

One embodiment of the device utilizes the reaction of sodium percarbonate, which reacts with water in the presence of the manganese catalyst. Another embodiment utilizes hydrogen peroxide of approximately 7.5% in an aqueous solution, and a rare earth metal such as reagent manganese dioxide or any number of other known catalysts, or combinations thereof. The two are mixed together, starting an exothermic reaction, which liberates pure oxygen. The reaction is $2H_2O_2$ (Aqueous solution)$\rightarrow$(catalyst) $2H_2O+O_2$. While this reaction is set forth as the preferred method of such a production it is to be distinctly understood that the invention is not limited thereto but may be variously embodied to meet the specific necessities of a user. Furthermore, while the present invention is described in the context of an oxygen producing device it is to be distinctly understood that the present invention may also be utilized in a variety of other types of gas production.

In one embodiment, the bag would be built and sterilized and the components then filled in the appropriate chambers. The tubing assembly would be stored with the flexible bladder, but not attached to the bag. This would allow the oxygen system to be stored until the time of use. This provides a self-pressurizing oxygen delivery system that may be utilized in a variety of circumstances including on the battlefield or other areas where access to water is unavailable. The invention is intended to be a disposable unit, therefore eliminating the need for excess storage. In addition, because the device is collapsible after use, the amount of space and weight required to haul the device is significantly decreased.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
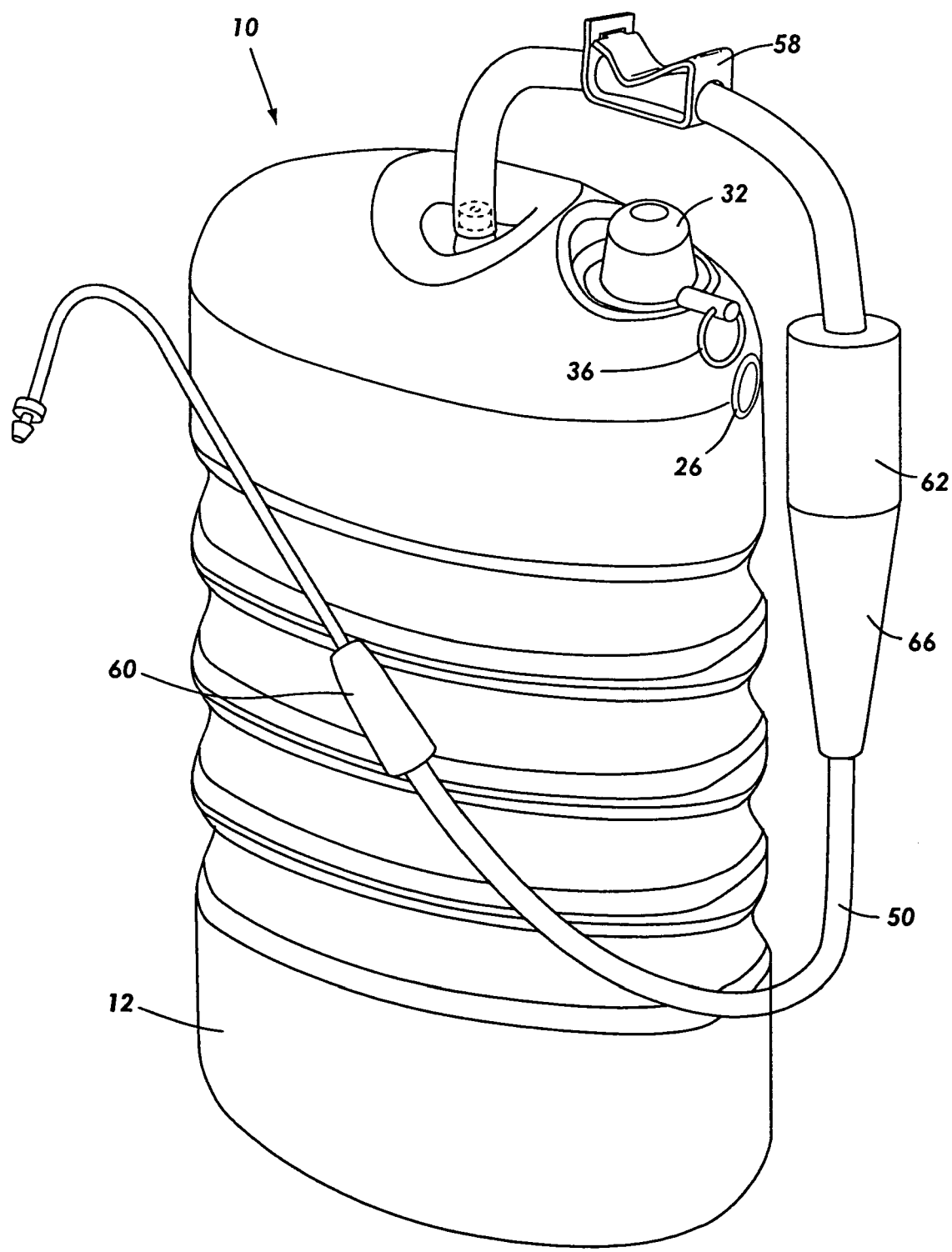
FIG. 1 is a perspective view of an embodiment of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Figure 2:
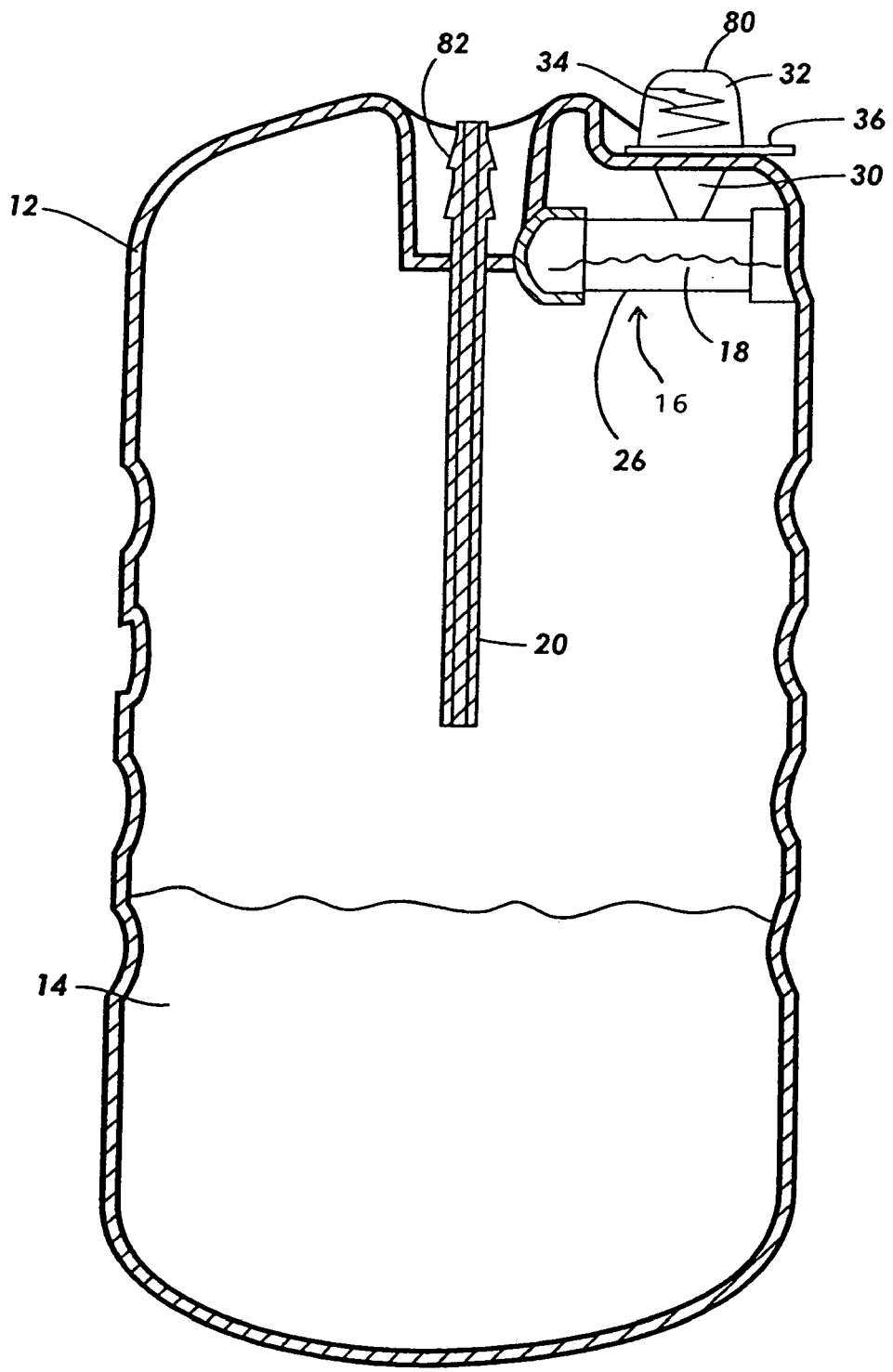
FIG. 2 is a cross-sectional view of the embodiment shown in FIG. 1.

Several preferred embodiments of the oxygen generation system of the invention are shown in the enclosed figures. FIG. 1 is one preferred embodiment of the system. It includes a reaction chamber 12, a delivery system that includes an air line clip 58, a liquid trap 62, a filter chamber 66, conduit 50, and an indicator chamber 60. On the top of the reaction chamber 12 is located a device for breaking the ampule 32 and a locking device 36. An ampule 26 is visible on the side of the reaction chamber 12 and internal components of the device are seen well in FIG. 2. FIG. 2 is a cross-sectional view showing the interior of the reaction chamber 12. Inside the reaction chamber 12 is a first reaction material 14. There is also a second chamber 16, which in this embodiment is a breakable ampule. Inside the ampule 26 is a second reaction material 18. Above the ampule 26 is located a plunger pin 30, which is used to break the breakable ampule. A locking device 36 is located below the plunger button 80. A hose barb 82 penetrates the wall of the reaction chamber 12 and extends into the reaction chamber as an oxygen release tube 20. The indicator chamber 60 contains a chemical that indicates when oxygen is flowing through the tube. The embodiment shown in any of the figures can also include a hydrophobic filter, a humidifying chamber, and/or a chemical filter, all mounted on the conduit leaving the face mask. These are optional devices placed in the path of out flowing oxygen generated in the oxygen generation system.

This oxygen generation unit can take a number of configurations and sizes, but a functional size for the reaction chamber has been found to be about one liter. With a one-liter volume, 300 to 350 mil of first reaction material 14 has been found to be appropriate. Seven to eight grams of the second reaction material 18 is appropriate for these volumes. When the second reaction material 18 is mixed with the first reaction material 14, a reaction takes place in which $O_2$ is generated. As $O_2$ is generated, it pressurizes the reaction chamber above the liquid level and exits the reaction chamber through the oxygen release tube 20 and out the hose barb. It then passes through the air line clip 58, the liquid trap 62, the filter chamber 66, and the indicator chamber 60. It would also be connected to a face mask or nasal canula, which is not shown in other drawings.

A number of materials can be used to generate oxygen, but the preferred mix is an aqueous solution of 7 to 10% hydrogen peroxide as first reaction material and reagent grade manganese as the second reaction material 18.

Figure 3:
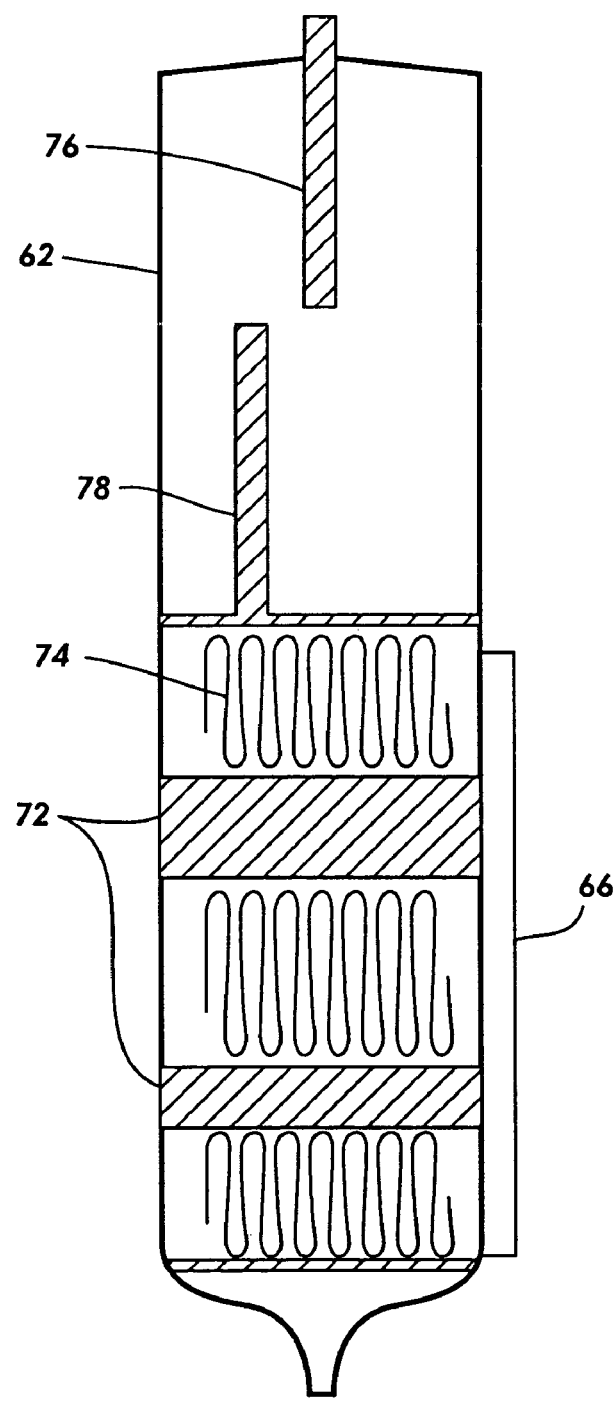
FIG. 3 is a cross-sectional view of a filter element of the invention.

FIG. 3 is a cross-sectional view that shows more detail of the filter that is shown in FIG. 1. The filter includes a liquid trap 62. An air line from the reaction vessel 12 enters the liquid trap 62 through a drip tube 76. There is an air tube 78 located below the drip tube and out of alignment with it. As oxygen gas enters the liquid trap, it passes through the drip tube and enters the air tube, and passes through the filter chamber 66. If any liquid enters through the drip tube 76, it is retained in the liquid trap 62, and only gas passes into the air tube 78. Inside the filter chamber 66 are located filtering material that removes contaminants from the oxygen, so that only pure oxygen exits the filter chamber 66 and continues on to the face mask 168. These filtering materials can take a number forms and these that are listed are the preferred form, although others are also suitable. The filter materials shown include several layers of activated charcoal 72 and other layers of foam or fibrous material 74. The preferred foam or fibrous material is Heat Moisture Exchanger Foam (HME). Another foam that has been used successfully is called biosponge, which is made of natural sponge.

An important feature of the design of the embodiment shown in FIGS. 1 and 2 is that the end of the oxygen release tube 20 is not submerged in liquid in any orientation. This results in a unit that can produce oxygen when it is upside down, lying flat on its side or standing upright. Thus, once oxygen generation is initiated, it would continue in any orientation.

In this embodiment, the second reaction material 18 and the first reaction material 14 are mixed by a user removing the locking cap 36 and then pressing the plunger button 80. This would depress the plunger pin 30 and break the material of the ampule 26. The material in the ampule 26 would then fall into the first reaction material or if the reaction chamber 12 is in another orientation, would mix with the first reaction material 14.

Figure 4:
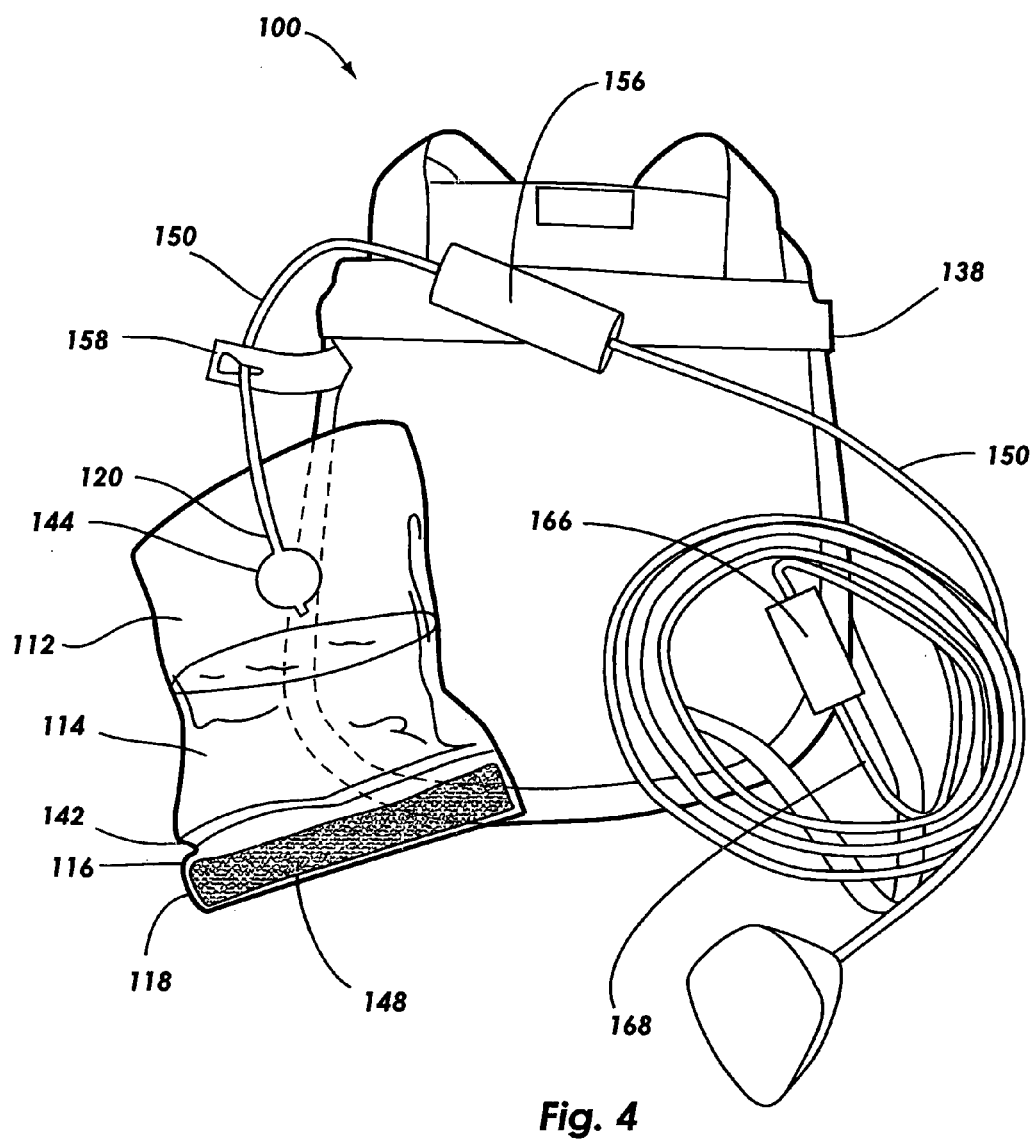
FIG. 4 is a second embodiment of the present invention.
Figure 5:
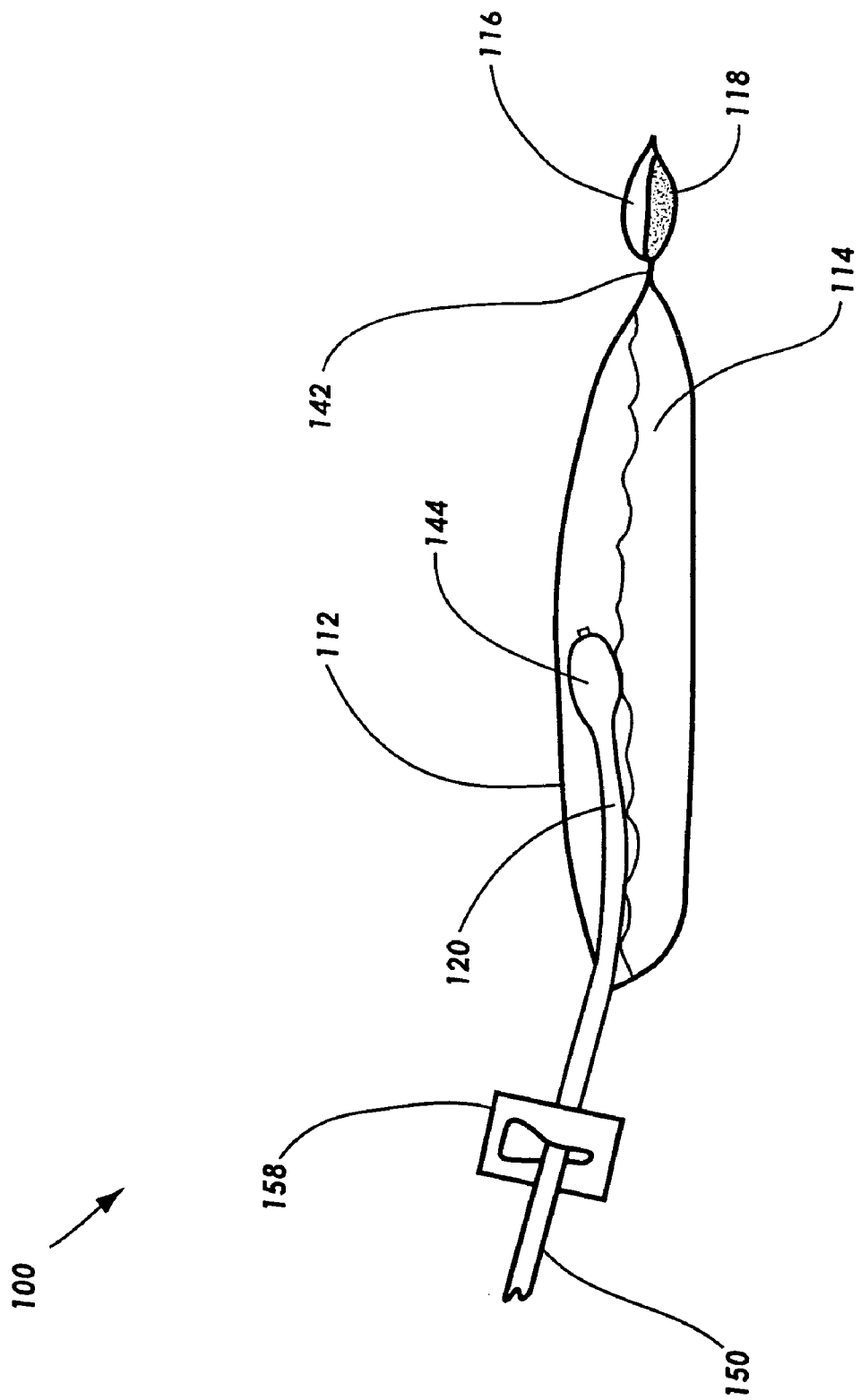
FIG. 5 is a side view of a third embodiment of the present invention.

Another preferred embodiment of the invention is shown in FIGS. 4, 5, and 6. Features of this embodiment are congruent with the previous embodiment, and are referred to by the same numbers, but in a 100 series. Thus, reaction chamber 12 is called 112. FIG. 4 shows an oxygen generation system 100, which includes a flexible bladder 148. The flexible bladder forms the reaction chamber 112. Within the reaction chamber 112 is the first reaction material 114. A second chamber is adjacent to and attached to the reaction chamber, and that is the second chamber 116. Inside the reaction chamber 116 is located a second reaction material 118. The two chambers are separated by a weak seal 142. When the reaction chamber 112 is squeezed, the weak seal 142 between the two chambers ruptures and allows the two materials to mix. Once the two materials mix, oxygen is generated, as in the previous embodiment. Inside the flexible bladder 148 is an oxygen release tube 120, to which is attached a float 144. The float 144 is provided so that the end of the oxygen release tube 120 is always above the surface of the liquid. This is accomplished by the oxygen release tube 120 having enough flexibility to allow the float to stay above the liquid level. As oxygen is generated, it exits through the oxygen release tube 120 and passes through an air line clip 158. The air line clip 158 would be removed in order to allow oxygen to pass through the conduit 150. An optional dehumidifier chamber is shown at 158. A filter chamber 166 is present and can take a number of configurations, including layers of activated charcoal and foam or fibrous filtration. From the filter chamber 166, the conduit 150 continues on to a face mask 168. The user applies the face mask 168 to his or another person's face to breath oxygen. The reaction is exothermic and thus an external carrying pouch 138 is useful. Once the reaction chamber 112 has been activated, it can be placed in the external carrying pouch 138 for carrying, keeping an upright, and preventing the heat of the reaction from burning a patient.

FIG. 5 shows the reaction vessel of this embodiment placed on its side. In this orientation, the float 144 keeps the oxygen release tube 120 above the level of the first reaction material 114. Shown is the adjacent second chamber 116 with its second reaction material 118. The two chambers are separated by a weak seal 142. Oxygen leaves the reaction chamber 112 via the conduit or tubing 150, after the air line clip 158 is removed.

Figure 6A:
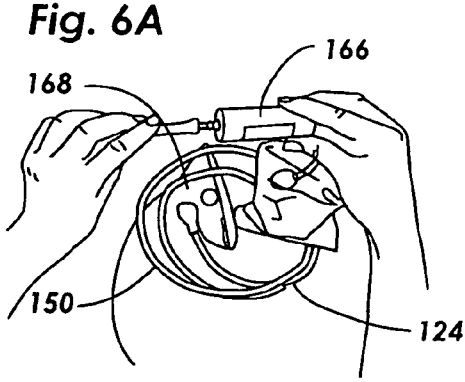
FIGS. 6A–6D shows the invention in use.
Figure 6B:
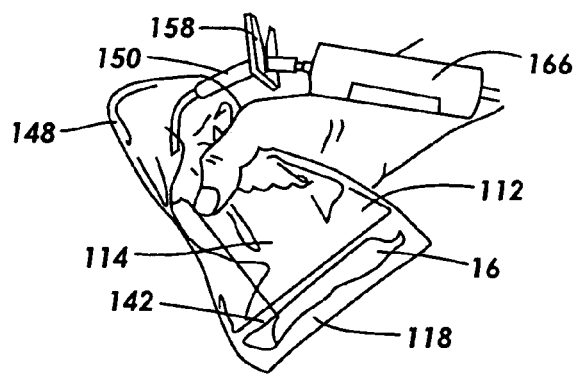

FIGS. 6a through 6d show this embodiment of the oxygen generation system in operation. In 6a, the conduit 150 with the attached face mask 168 is attached to the filter unit 166. Thus, all the components are joined. In FIG. 6b, the user applies pressure to the reaction chamber 112 and breaks the weak seal 142. When that occurs, the first reaction material 114 and the second reaction material 118 mix together. Upon mixing, oxygen is generated. At that point the air line clip 158 is removed from the conduit 150 and oxygen begins to flow out of the reaction chamber 112 and through the filter 166.

Figure 6C:
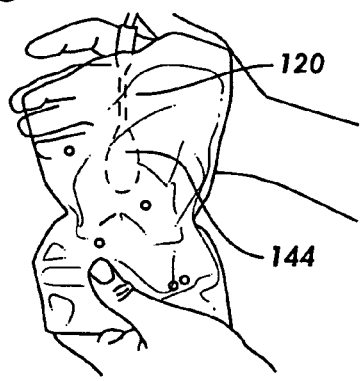

In FIG. 6c, the float 144 attached to the oxygen release tube 120 is visible and serves to keep the oxygen release tube 120 above the level of the liquid at all times.

Figure 6D:
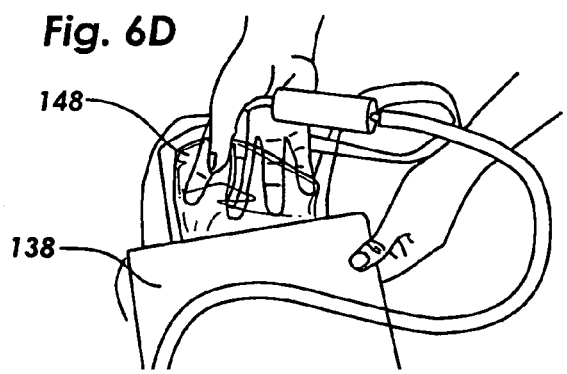

In FIG. 6d, the flexible bladder 146 is placed into the external carrying pouch 138, from which oxygen continues to be generated and flow to the face mask 168.

Figure 7:
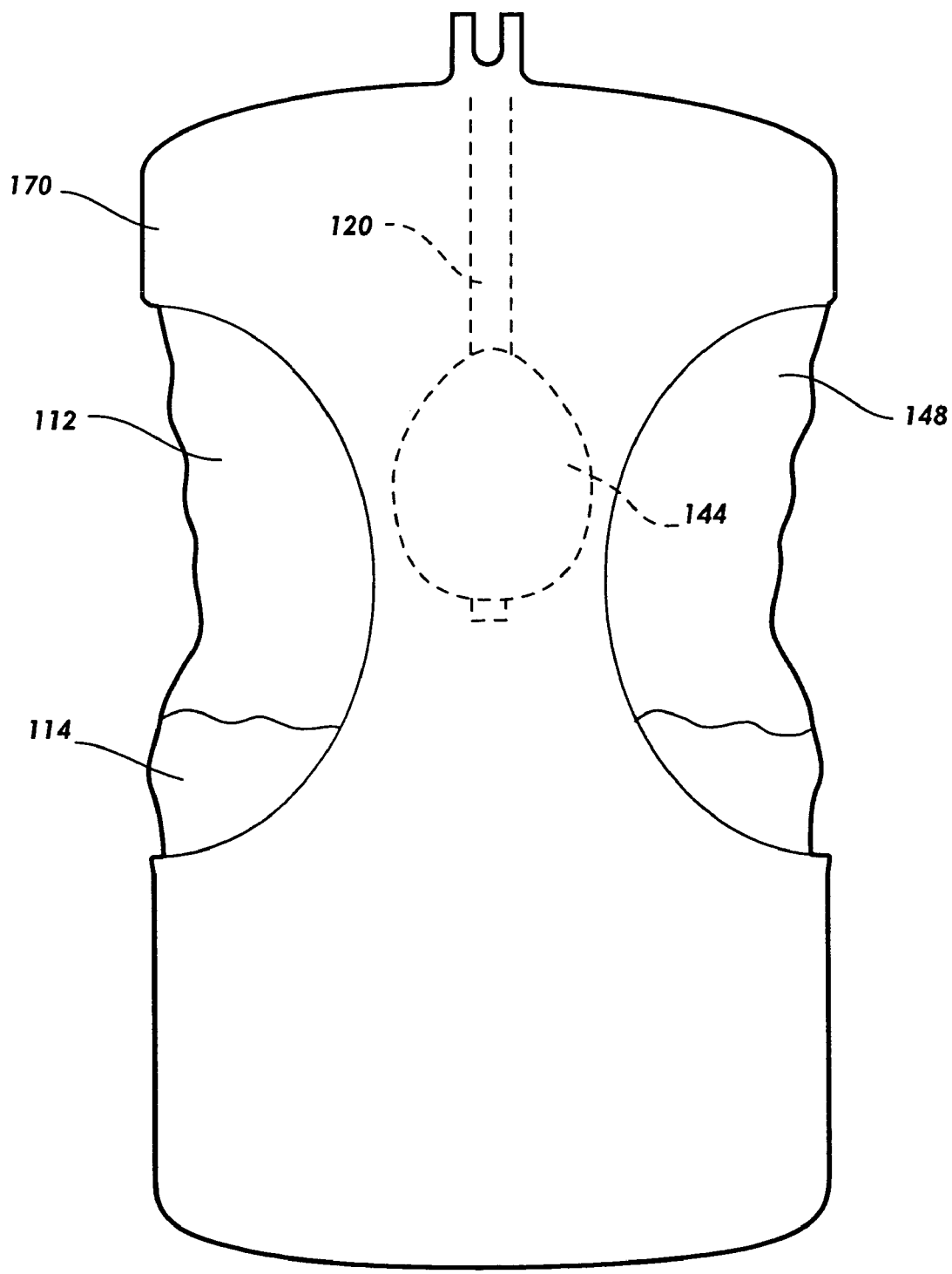
FIG. 7 is a front view of an embodiment of the present invention.
Figure 8:
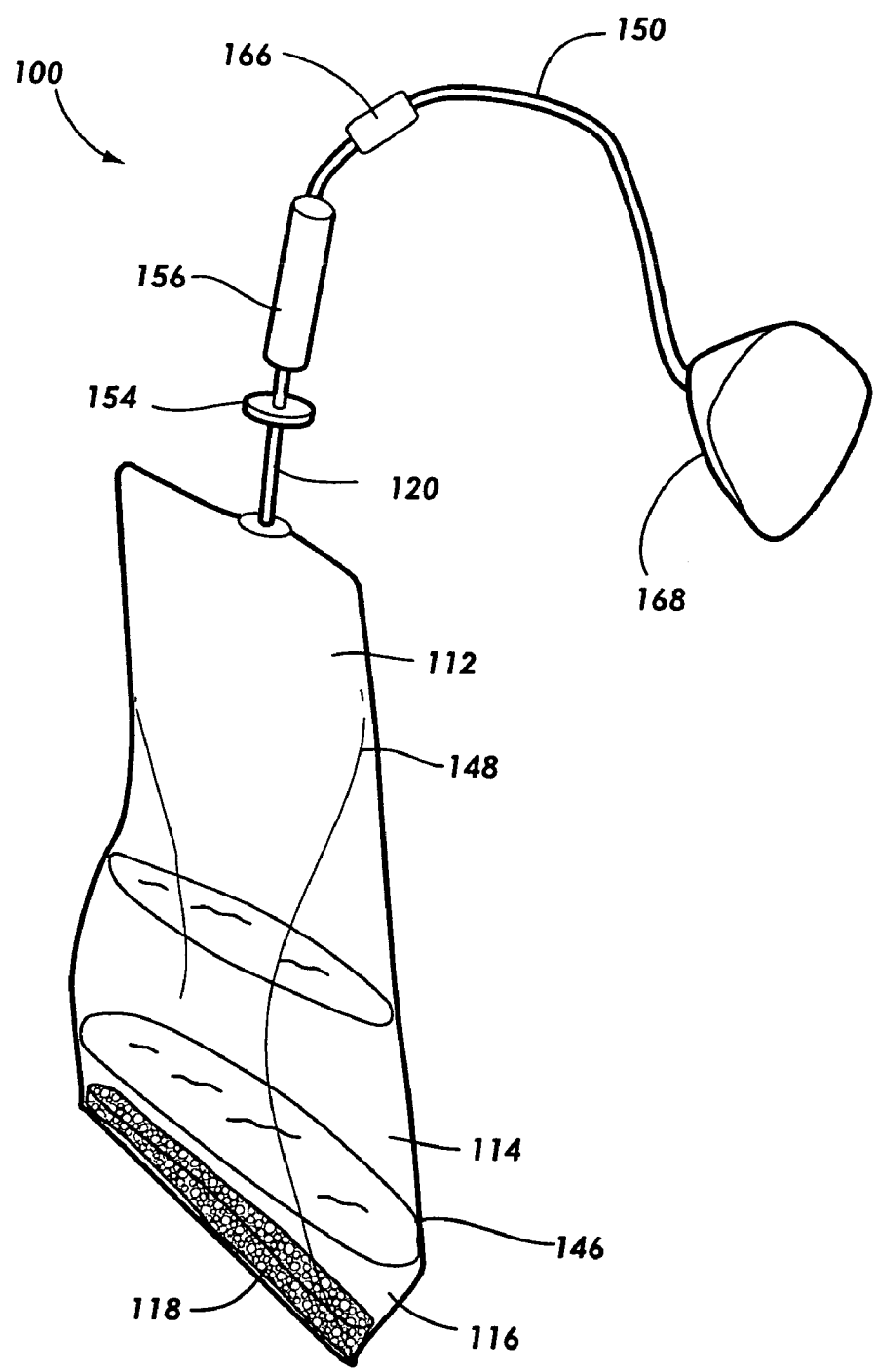
FIG. 8 is another embodiment of the present invention.

Another embodiment of the invention is shown in FIG. 7. FIG. 7 shows the flexible bladder 148 of the previous embodiment housed within a rigid outer container 170. This embodiment operates basically the same as the previous embodiment, with the reaction chamber 112 being squeezed to rupture a weak seal 142, thus allowing the mixing of the first reaction material 114 and the second reaction material 118. An oxygen release tube 120 is shown in this device, attached to a float 144. The oxygen release tube 120 of this device passes through the outer rigid container 170 and is held firmly in place by the outer rigid container 170. Thus, this device holds the oxygen release tube 120 in a position so that it is not submerged in liquid in any orientation. The use of an air line clip, an indicator chamber, liquid trap, check valve, filter chamber, conduit, and air mask are all the same with this embodiment.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

We claim:

1. A portable oxygen generating system for providing breathing oxygen said system comprising:
   a reaction chamber containing a pre-measured volume of a first reaction material which partially fills said reaction chamber;
   a second chamber adjacent to said reaction chamber, containing a pre-measured volume of a second reaction material, said first and second materials selected so that oxygen is generated when said first material and said second materials are mixed;
   an oxygen release tube positioned within said reaction chamber to be above the level of said first material, when the reaction chamber is in any spatial orientation;
   an activation means, which is configured to immediately activate oxygen generation by opening said second chamber to allow immediate mixing of said second material with said first material, resulting in immediate and continuous oxygen production from mixing and subsequent reaction; and
   a delivery device configured to deliver oxygen created within said reaction chamber to a user;
   wherein said portable oxygen generating system is configured for activation and operation in any spatial orientation.

2. The portable oxygen generating system of claim 1 in which said reaction chamber is a semi rigid material.

3. The portable oxygen generating system of claim 2 in which said second chamber is a breakable ampule containing said second reaction material.

4. The portable oxygen generating system of claim 3 in which said ampule is supported in an ampule bracket within the reaction chamber.

5. The portable oxygen generating system of claim 3 in which said activator means is a device for breaking the ampule.

6. The portable oxygen generating system of claim 5 in which the device for breaking the ampule is a plunger pin.

7. The portable oxygen generating system of claim 6 in which the device for breaking the ampule is spring loaded.

8. The portable oxygen generating system of claim 6 in which the device for breaking the ampule has a locking device for preventing unwanted activation.

9. The portable oxygen generating system of claim 1, which further includes an external carrying pouch for storing and transporting, and as a heat shield for said portable oxygen generating system.

10. The portable oxygen generating system of claim 1 in which said oxygen release tube extends from a reaction chamber wall to the approximate center of the reaction vessel, and includes a tube opening, and because said first material only partially fills said reaction vessel, said tube opening remains above the level of the first material when the reaction vessel is in any spatial orientation.

11. The portable oxygen generating system of claim 10 in which said oxygen release tube is attached at one end to said reaction chamber wall.

12. The portable oxygen generating system of claim 1 in which said reaction chamber is a flexible pouch enclosed in a semi-rigid external case.

13. The portable oxygen generating system of claim 12 in which said second chamber is a chamber in a flexible pouch, and said reaction chamber is a chamber in said flexible pouch.

14. The portable oxygen generating system of claim 12 in which the activation means is a seal between the second chamber and said reaction chamber, which is opened by squeezing the flexible pouch.

15. The portable oxygen generating system of claim 12 in which said oxygen release tube extends from a reaction chamber wall to the approximate center of the reaction vessel, and includes a tube opening, and because said first material only partially fills said reaction vessel, said tube opening remains above the level of the first material when the reaction vessel is in any spatial orientation.

16. The portable oxygen generating system of claim 15 in which the oxygen release tube is a flexible tube that includes a float.

17. The portable oxygen generating system of claim 1 in which said reaction chamber is a flexible pouch.

18. The portable oxygen generating system of claim 1 wherein said delivery device further comprises: a conduit having a first end configured for connection to said air release tube and a second end configured to attachment to an oxygen delivery mask.

19. The portable oxygen generating system of claim 18 wherein said delivery device further comprises a chemical filter located within said conduit between said first end and said second end, said chemical filter configured to allow passage of oxygen from a flexible bladder to said mask and to prevent passage of other gases or odors from said bladder through said conduit.

20. The portable oxygen generating system of claim 18 wherein said delivery device further comprises a hydrophobic filter located within said conduit between said first end and said second end, said hydrophobic filter configured to allow passage of oxygen from a flexible bladder to said mask and to prevent passage of liquid from said bladder through said conduit.

21. The portable oxygen generating system of claim 12 wherein said delivery device further comprises a chemical filter located within said conduit between said first end and said second end, said chemical filter configured to allow passage of oxygen from said flexible bladder to said mask and to prevent passage of other gases or odors from said bladder through said conduit.

22. The portable oxygen generating system of claim 19 in which said chemical filter contains activated charcoal, for absorption of odors and gases other than oxygen.

23. The portable oxygen generating system of claim 1 wherein said first material is selected liquid from the group of compounds comprising sodium percarbonate, hydrogen peroxide, potassium percarbonate, and distilled water.

24. The portable oxygen generating system of claim 1 wherein said second material is a catalyst selected from the group comprising manganese, dioxide, charcoal, and rare earth metals.

25. The portable oxygen generating system of claim 1 in which said first material is hydrogen peroxide.

26. The portable oxygen generating system of claim 25 in which said hydrogen peroxide is a solution of 5–10% peroxide.

27. The portable oxygen generating system of claim 24 wherein said second material is manganese dioxide powder.

28. The portable oxygen generating system of claim 18 wherein said delivery device further comprises a humidifier chamber positioned between said hydrophobic chamber and said flexible bladder.

29. The portable oxygen generating system of claim 28 wherein said delivery device further comprises a check valve positioned between said humidifier chamber and said flexible bladder.

30. The portable oxygen generating system of claim 29 wherein said delivery device further comprises a tubing clamp positioned between said check valve and said flexible bladder said tubing valve configured to control the flow of oxygen out of said flexible bladder.

* * * * *